(12) United States Patent
Maizlin et al.

(10) Patent No.: US 8,485,448 B2
(45) Date of Patent: Jul. 16, 2013

(54) TAMPER-PROOF IDENTIFICATION DEVICE PARTICULARLY USEFUL AS A BRACELET TO BE APPLIED TO THE WRIST OR ANKLE OF A PATIENT

(75) Inventors: Yaron Maizlin, Ramat-Yishai (IL); Shlomo Ayanot, Mitzpe Adi (IL); Roni Amrami, Yokneam (IL)

(73) Assignee: Itamar Medical Ltd., Caesarea (IL)

( * ) Notice: Subject to any disclaimer, the term of this patent is extended or adjusted under 35 U.S.C. 154(b) by 0 days.

(21) Appl. No.: 13/148,317

(22) PCT Filed: Feb. 4, 2010
(Under 37 CFR 1.47)

(86) PCT No.: PCT/IL2010/000103
§ 371 (c)(1),
(2), (4) Date: Nov. 14, 2011

(87) PCT Pub. No.: WO2010/089745
PCT Pub. Date: Aug. 12, 2010

(65) Prior Publication Data
US 2012/0132717 A1    May 31, 2012

Related U.S. Application Data

(60) Provisional application No. 61/150,768, filed on Feb. 8, 2009.

(51) Int. Cl.
*G06K 19/06*    (2006.01)

(52) U.S. Cl.
USPC .......................................... 235/492; 235/487

(58) Field of Classification Search
USPC .................................................. 235/492, 487
See application file for complete search history.

(56) References Cited

U.S. PATENT DOCUMENTS

| | | |
|---|---|---|
| 6,346,886 B1 | 2/2002 | De La Huerga |
| 6,693,543 B1 | 2/2004 | Stephenson et al. |
| 2003/0173408 A1 | 9/2003 | Mosher et al. |
| 2007/0120687 A1 | 5/2007 | Lerch et al. |
| 2007/0144047 A1 | 6/2007 | Singh |
| 2008/0290176 A1 | 11/2008 | Fleet |

FOREIGN PATENT DOCUMENTS

| | | |
|---|---|---|
| WO | WO 2006/093657 | 9/2006 |
| WO | WO 2010/089745 | 8/2010 |

OTHER PUBLICATIONS

International Preliminary Report on Patentability Dated Aug. 18, 2011 From the International Bureau of WIPO Re. Application No. PCT/IL2010/000103.
International Search Report and the Written Opinion Dated Feb. 23, 2007 From the International Searching Authority Re: Application No. PCT/IL2010/00103.

*Primary Examiner* — Allyson Trail

(57) ABSTRACT

A tamper-proof identification device is characterized in that it includes a non-stretchable band and an electrically-conductive loop having a first gap bridged by an electronic identification chip and a second gap defined by a pair of electrical terminals for connection to a data processor, such that the identification device protects against removal by stretching as well as by severing.

17 Claims, 3 Drawing Sheets

TAMPER-PROOF IDENTIFICATION DEVICE PARTICULARLY USEFUL AS A BRACELET TO BE APPLIED TO THE WRIST OR ANKLE OF A PATIENT

RELATED APPLICATIONS

This application is a National Phase of PCT Patent Application No. PCT/IL2010/000103 having International filing date of Feb. 4, 2010, which claims the benefit of priority of U.S. Provisional Patent Application No. 61/150,768 filed on Feb. 8, 2009. The contents of the above applications are all incorporated herein by reference.

FIELD AND BACKGROUND OF THE INVENTION

The present invention relates to a tamper-proof identification device applicable to a body part of a subject for identifying the subject. The invention is particularly useful for application around the wrist or ankle of a patient for performing ambulatory diagnostic studies of patients, and is therefore described below with respect to such an application, but it will be appreciated that the invention could also be used in other applications.

Governments, insurance companies, employers of public transportation, truck drivers, and the like are seeking a simple way of performing ambulatory diagnostic studies for various physiological conditions which can affect a person's alertness while driving, controlling heavy equipment, etc. Examples of such physiological conditions include obstructive sleep apnea (OSA), and other sleep-related disordered breathing conditions, which may cause road accidents, misoperation of machinery, etc. One of the main problems involved, however, is to assure that the person carrying the diagnostic device is actually the person intended to be monitored. Various types of identification bracelets have been provided for this purpose, as described for example in U.S. Pat. No. 5,883,576.

OBJECTS AND BRIEF SUMMARY OF THE INVENTION

An object of the present invention is to provide an identification device which is effectively tamper-proof. Another object of the invention is provide such a tamper-proof identification device particularly useful as a bracelet to be applied to the wrist, ankle, or other body region such the neck or torso of a patient. A further object is to provide such a tamper-proof identification device wherein its effective size is adjustable to fit the particular body region so as to prevent its removal by simply dragging it over the local terminal extremity of the body A still further object is to provide such a tamper-proof identification device which is of a simple construction requiring relatively few parts which can be produced and assembled in volume and at low cost.

According to a broad aspect of the present invention, there is provided a tamper-proof identification device, comprising: a flexible band configured, dimensioned and fastenable at regions of its opposing ends to enclose and fit a body part of a wearer to identify the wearer; a flexible, electrically-conductive pathway carried by said band to define an electrically-conductive loop when regions of the opposing ends of the band are fastened together to enclose and fit the body part; an electronic identification chip carried by said band and electrically connected to said loop; and a pair of electrical terminals carried by said band and electrically connected to said loop for connection to a data processor, such that electrical communication may be established between said electronic identification chip and said data processor via said electrically-conductive loop when the data processor is connected to said pair of electrical terminals, but severing said band will interrupt said electrically-conductive loop and thereby prevent establishing electrical communication between the electronic identification chip and the data processor; characterized in that said flexible band is a non-stretchable band to prevent removal of the identification device by stretching it over said body part; and in that said electrically-conductive loop has a first gap therein bridged by said electronic identification chip, and a second gap therein defined by a pair of electrical terminals for connection to said data processor, such that said identification device protects against removal by stretching as well as by severing.

According to further features in the preferred embodiments of the invention described below, the band is made of sheet material and is severable by cutting, such as by a scissors. More particularly, the band includes an insulating base sheet formed with a printed circuit defining the electrically-conductive pathway, and an insulating overlying sheet bonded to the base sheet, the electronic identification chip being bonded between the base and overlying sheets. The electronic identification chip is for example, a read-only memory or EPROM chip, or a random access memory chip bonded between the base and overlying sheets.

According to further features in the described preferred embodiments, the band is formed with a series of holes along its length, and the device includes a fastener to be inserted through aligned holes at the opposite ends of the band to enclose and fit the body part of the wearer.

In two described embodiments, the fastener is integrally formed with the band and includes two parts, one part being formed with a pin having a locking element, the other part being formed with a socket for receiving the pin and having a locking recess for receiving the locking element of the pin in a manner to prevent removal of the pin from the socket, once received therein, without damaging one or both of the parts. The band includes a main section formed with the series of holes, and with an end section formed at one end of the main section and carrying the two parts of the fastener. In these embodiments, the pair of electrical terminals are also designed so as also to serve as mounting posts for mounting a tag visually identifying the wearer.

Also in these preferred embodiments, the end section is formed perpendicularly to, and at one end of, the main section of the band. The end section is foldable along a line midway between the two parts of the fastener to permit the pin of the one part to be received through a selected hole in the main section of the band, and then through the socket in the other part of the fastener.

In another described preferred embodiment, the end section is formed coaxially with, and at one end of, the main section of the band.

In all the described preferred embodiments, the band is configured and dimensioned to define a bracelet to enclose and fit the wrist, ankle or other body part of the wearer. Also, the identification device further includes a data processor connectable to the pair of electrical terminal for establishing communication with the electronic identification chip. The data processor could, in turn, be connected to a physiological condition-monitoring device, such as a finger-probe, pulse oximeter, respiration monitor or the like, which records data concerning the patient and at the same time assures that such data will be identified with respect to the specific patient being monitored.

As will be described more particularly below, such an identification device can be constructed in volume, at low cost, and to obviate the need of any electrical power supply. Moreover, it assures that once the bracelet is applied to a particular individual, the data gathered will be from that particular individual, and from no one else, and thus prevents even accidental errors in identifying the source of the recorded data. It further assures that any attempt to remove or otherwise tamper with the bracelet will result in an invalidation of the data produced.

Such an identification device is thus particularly useful for monitoring various physiological conditions of a person which can affect a person's alertness while driving, controlling heavy equipment, etc. It is also useful in other personal monitoring systems, for example to detect an attempted departure from a bed or hospital premises, compliance with a protective order, etc. The identification device also assures that particular data taken from a subject will always be identified with the particular subject, so that such data cannot be accidentally or intentionally ascribed to another subject.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

For purposes of example, the drawings illustrate the invention embodied in the form of an identification bracelet to be applied around the wrist or ankle of a patient. It will be appreciated, however, that the invention can also be embodied in other types of devices for application around other body parts of the patient, such as the upper arm, thigh, torso, waist, or neck, in order to identify the patient.

Figure 1:
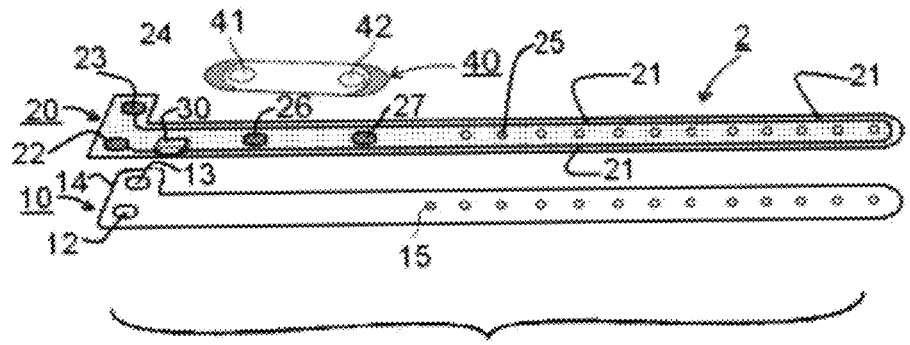
FIG. 1 illustrates the main parts of one form of identification and tamper-proof bracelet constructed in accordance with the present invention, the parts being shown in their flat condition.
Figure 2:
FIG. 2 is a side elevational view of the bracelet of FIG. 1 in its flat condition.
Figure 3:
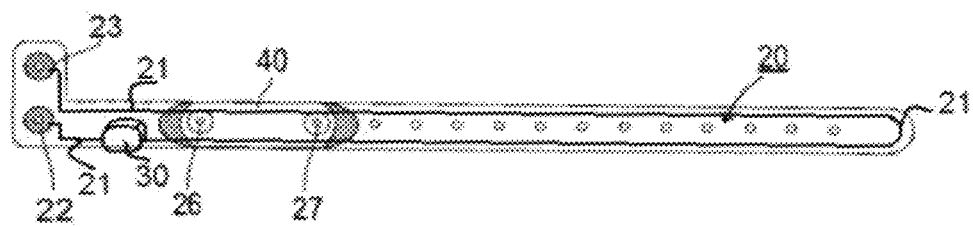
FIG. 3 is a top plan view of the bracelet of FIG. 1 in its flat condition.

FIG. 1 schematically illustrates the bracelet as including a band 2 constructed of two layers, namely an insulating base layer, generally designated 10, and a printed-circuit layer 20 overlying the base layer 10. The printed circuitry is formed on the under surface of layer 20 so that it is sandwiched between the two layers when bonded together.

The printed circuitry formed on the under surface of layer 20 includes a flexible, electrically-conductive pathway defining, when regions of the opposing ends of the band are fastened together to enclose and fit the body part (e.g. wrist or ankle) of a person, an electrically-conductive loop 21 having first and second gaps in the loop.

Figure 5:
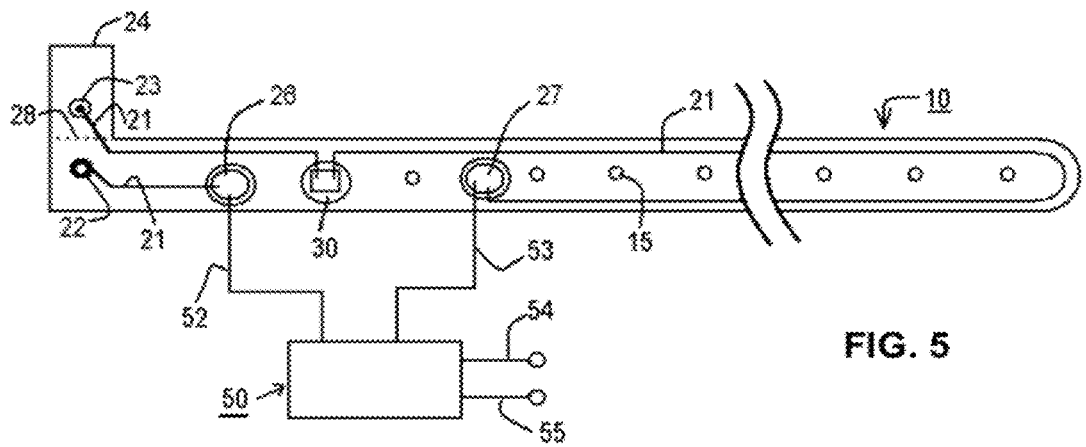
FIG. 5 is a schematical electrical circuit diagram illustrating the main parts in the identification device of FIGS. 1-4.

As best seen in FIG. 5, one of the gaps is occupied by an electronic identification chip 30 which identifies the respective bracelet, and therefore the wearer of that bracelet. A pair of electrical terminals 22, 23, which serve as fastening elements as will be described below, are formed in a perpendicular end section 24 at one end of the main section 25 of printed circuit layer 20.

A further pair of electrical terminals 26, 27 are formed in the main body section 25 of electric circuit layer 20 adjacent to the end section 24. Terminals 26, 27 are electrically connected to loop 21 and define the second gap in the loop for connection to a data processor (50, FIG. 5).

Both layers 10 and 20 are made of a flexible and non-stretchable sheet material, which is severable, e.g., by scissors, to enable quick removal of the bracelet after it has performed its identification function for the respective patient. As will be described below, the bracelet is tamper-proof such that severing the bracelet will automatically disable it from performing its identification function.

Insulating base layer 10 is a continuous strip formed with two holes 12, 13 in an end section 14 at one end of the main section of the layer. Layer 10 is further formed with a plurality of small holes 15 aligned with corresponding holes 25 in layer 20, to enable the strip to be wrapped around the wrist or ankle of the patient, and to be secured in the form of a bracelet thereon.

The bracelet is applied to the subject by wrapping the main section 25 of the bracelet around the subject's wrist, ankle, or other body region, and inserting appropriate holes 15 and 25 at the right hand of the bracelet into fastener element 22 at the left end of the bracelet, to suit the size of the body part. The perpendicular end section 24 of the bracelet is then folded about fold line 28 (FIG. 5) to seat fastener 23 into fastener 22, to thereby close the bracelet.

Figure 4:
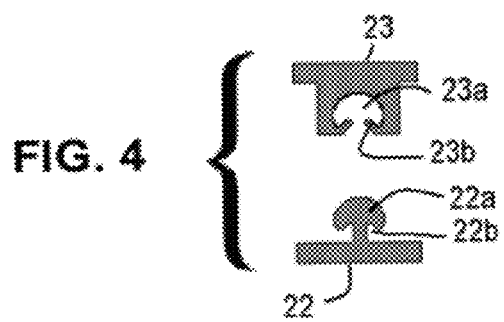
FIG. 4 is a sectional view of a two-part fastener that can be used to fasten together the two ends of the band of FIGS. 1-3 in a manner which prevents removal of the fastener without destroying it.

The fastener elements 22, 23 are constructed such that, when closed in the above manner, they cannot be opened without breaking one or both parts of this fastener. FIG. 4 illustrates a construction that may be used for this purpose. Thus, as shown in FIG. 4, fastener element 22 includes a pin 22a formed at its base with a locking recess 22b; and fastener element 23 includes a socket 23a receiving pin 22a, and with a locking element 23b seatable within recess 22b, to thereby lock the two parts together against separation except by destroying one or both parts.

FIG. 5 is a diagram schematically illustrating the circuit in the bracelet of FIGS. 1-4. In this embodiment, the two fastener elements 22, 23 are made of metal and are electrically connected within the loop 21, such that, when fastener element 23 is inserted into fastener element 22, by folding along fold line 28, the electrically-conductive pathway carried by the bracelet defines an electrically-conductive loop 21 which extends from one end of the band to the other around fastener elements 22 and 23. Such a loop includes two gaps; namely a first gap which is bridged by electronic identification chip 30, and a second gap defined by the two terminals 26, 27. The latter terminals are connectable to a data processor 50 by connecting leads 52, 53. The data processor 50 may in turn have leads, e.g. 54, 55, to various monitors, such as a finger-probe, a temperature sensor, a pulse-rate sensor, or any other sensors for sensing desired physiological conditions of the subject to be monitored.

Electronic identification chip 30 is preferably is a read-only memory (ROM) identifying the respective bracelet, and thereby the wearer of the bracelet, in a tamper-proof manner, such that severing the bracelet after its identification function has been performed, will automatically disable the bracelet from being used with respect to another patient.

The bracelet defined by layers 10 and 20 further includes an identification tag, generally designated 40 (FIG. 1), containing the wearer's name, or otherwise identifying the patient in a visual manner. Tag 40 is formed with openings 41, 42 at its opposite ends, to permit mounting the tag to the bracelet via the electrical terminals 26, 27.

Figure 6:
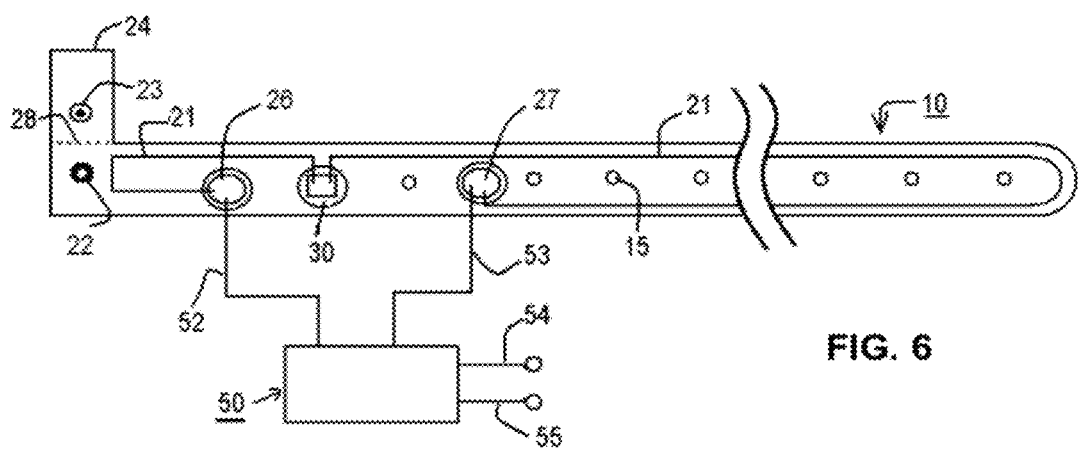
FIG. 6 is a schematical electrical circuit diagram similar to that of FIG. 5 but illustrating a modification in the electrical circuit.

FIG. 6 is a schematic diagram illustrating a modification in the electrical circuit illustrated in FIG. 5, namely in that the two fastener elements 22, 23 carried by the end extension 24 are not electrically connected to the electrically-conductive loop 21. Therefore, according to this modification, while forcing these two fastener elements apart will not disable the bracelet from identifying the wearer, the fact that at least one of the fastener elements 22, 23 is broken, will be apparent and will therefore invalidate the bracelet from being used for identification purposes. In all other respects, the bracelet of FIG. 6 is constructed and operates in the same manner as described above with respect to FIGS. 1-5, and therefore the same reference numerals have been used to identify the corresponding elements.

Figure 7:
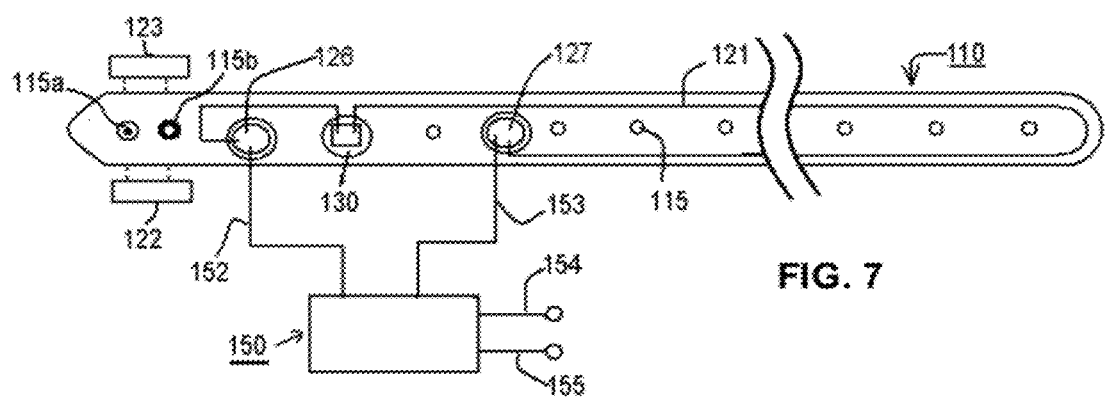
FIG. 7 is a further schematical electrical circuit diagram similar that of FIG. 5 but illustrating a modification in the construction of the identification device.

FIG. 7 diagrammatically illustrates a further embodiment of the invention, similar to that of FIG. 6, except that the end section of the bracelet carrying the fastener element is coaxial with, rather than perpendicular to, the main section of the bracelet. Also, the fastener elements are separate elements, rather than being integrally formed with the bracelet. For the sake of convenience, those elements in FIG. 7, which generally correspond to the elements discussed above in FIGS. 1-6, carry the same reference numerals but increased by "100".

Thus, the bracelet in FIG. 7, therein generally designated 110, includes a flexible, non-stretchable, severable band configured, dimensioned and fastenable at regions of its opposing ends to enclose and fit the wearer's wrist, ankle, or other body parts. It also includes a flexible, electrically-conductive pathway carried by the band to define, when regions of the opposing ends of the band are fastened together to enclose and fit the body parts, an electrically-conductive loop 121 having first and second gaps. An electronic identification chip 130 is electrically connected to said loop across one of the gaps; and a pair of electrical terminals 126, 127, spaced by the other gap, electrically connect the loop to the data processor 150 via leads 152, 153. The data processor 150 may in turn be connected to one or more sensors for sensing various physiological conditions of the wearer of the bracelet, as indicated by leads 154, 155.

Bracelet 110 is also formed with a series of holes 115 to permit application of the bracelet to the body part of the wearer according to the diameter of the respective body part.

In the embodiment illustrated in FIG. 7, the end section of the bracelet 110, used for fastening the bracelet around the body part, is occupied by two holes 115a, 115b. These holes cooperate with separate fastener elements 122, 123, and the appropriate holes 115 at regions of the opposing ends of the bracelet, to secure the bracelet ends according to the size of the part to be enclosed and fitted.

Figure 9:
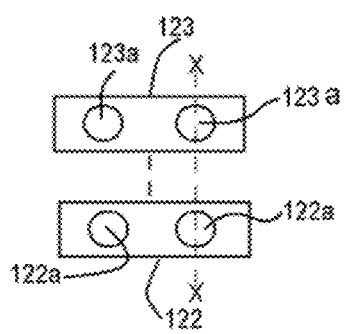
FIG. 9 is a top view illustrating the two parts of the fastener in FIG. 7.
Figure 10:
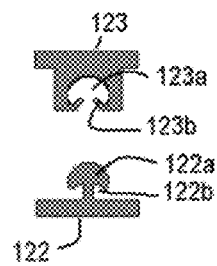
FIG. 10 is a sectional view along line X - - - X of FIG. 9.

Fastener parts 123, 124 are more particularly illustrated in FIGS. 9 and 10. As shown by the sectional view in FIG. 10, each of the two fastener parts 122 and 123 include two sections in side-by-side relationship, with each section of substantially the same construction as described above with respect to FIG. 4. Thus, fastener part 122 includes two pins 122a, each of the same construction as pin 22a in FIG. 4; and fastener part 123 includes two sockets 123a, each of the same construction as sockets 23a in FIG. 4.

Figure 8:
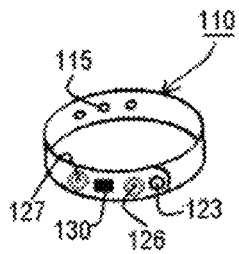
FIG. 8 illustrates the bracelet of FIG. 7 in its closed condition when enclosing the wrist or ankle of the subject.

It will thus be seen that when the two holes 115a, 115b in the coaxial end section of the bracelet 110 are aligned with the appropriate holes 115 in the main section of the bracelet, the two fastener elements 122, 123 may be located on opposite sides of the bracelet and these may be pressed together, via holes 115a, so as to close in a non-separable manner as described above with respect to FIG. 4, and as schematically shown in FIG. 8.

Figure 11:
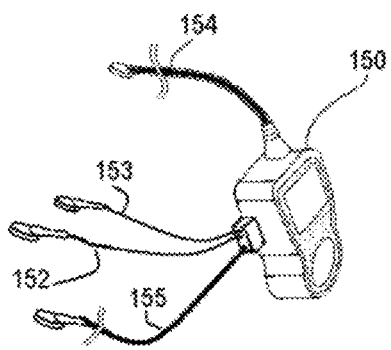
FIG. 11 illustrates the data processor to be applied to the bracelet when worn by the subject.
Figure 12:
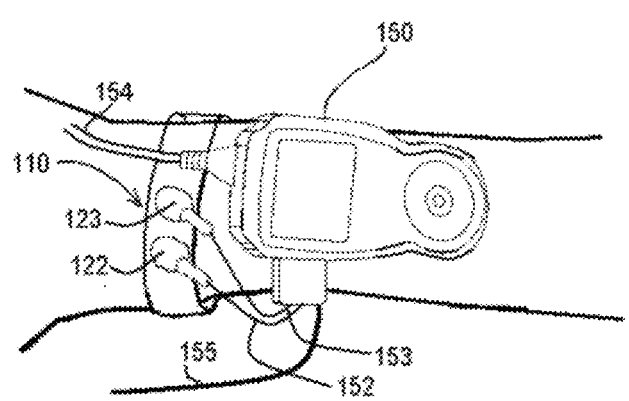
FIG. 12 illustrates the data processor as applied to the bracelet enclosing the subject's wrist or other body region.

FIG. 11 illustrates the data processor 150 per se, including the leads 152, 153 for application to the electrical terminals 126, 127 of the bracelet, and further leads, e.g., 154, for connection to one or more sensors for sensing various physiological conditions of interest. FIG. 12 illustrates the data processor applied to the bracelet.

It will thus be seen that the embodiment illustrated in FIGS. 7-12 also provide tamper-proof protection when gathering data or processing data with respect to a particular wearer, identified by the electronic identification chip 130 of the bracelet. However, if the bracelet is severed, e.g. by scissors, this will effectively interrupt the connection of the bracelet to the data processor 150. In addition, the illustrated bracelet cannot be opened by separating fastener elements 122, 123, to enable the bracelet to be applied to another person, since separation of the two fastener elements will result in the breakage of one or both fastener elements, which will clearly be visible.

While the invention has been described with respect to several preferred embodiments, it will be appreciated that these are set forth merely for purposes of example, and that many other variations, modifications and applications of the invention may be made. Likewise, additional features known to the art to be useful in other personal monitoring systems, for example GPS and wireless communication features, could be usefully added to the invention.

What is claimed is:

1. A tamper-proof identification device, comprising:
  a flexible band configured, dimensioned and fastenable at regions of its opposing ends to enclose and fit a body part of a wearer to identify the wearer;
  a flexible, electrically-conductive pathway carried by said band to define an electrically-conductive loop when regions of the opposing ends of the band are fastened together to enclose and fit the body part;

an electronic identification chip carried by said band and electrically connected to said loop;

and a pair of electrical terminals carried by said band and electrically connected to said loop for connection to a data processor, such that electrical communication may be established between said electronic identification chip and said data processor via said electrically-conductive loop when the data processor is connected to said pair of electrical terminals, but severing said band will interrupt said electrically-conductive loop and thereby prevent establishing electrical communication between the electronic identification chip and the data processor;

characterized in that said flexible band is a non-stretchable band to prevent removal of the identification device by stretching it over said body part; and in that said electrically-conductive loop has a first gap therein bridged by said electronic identification chip, and a second gap therein defined by a pair of electrical terminals for connection to said data processor, such that said identification device protects against removal by stretching as well as by severing.

2. The identification device according to claim 1, wherein said band is made of sheet material and is severable by cutting.

3. The identification device according to claim 1, wherein said band includes an insulating base sheet formed with a printed circuit defining said electrically-conductive pathway, and an insulating overlying sheet bonded to said base sheet, said electronic identification chip being bonded between said base and overlying sheets, both said insulating base sheet and said insulating overlying sheet being non-stretchable.

4. The identification device according to claim 3, wherein said electronic identification chip is a read-only memory chip bonded between said base and overlying sheets.

5. The identification device according to claim 3, wherein said band is formed with a series of holes along its length, and said device includes a fastener to be inserted through aligned holes at regions of the opposing ends of the band to enclose and fit said body part of the wearer.

6. The identification device according to claim 3, wherein said fastener is formed integrally with said band and includes two parts, one part being formed with a pin having a locking element, the other part being formed with a socket for receiving said pin and having a locking recess for receiving said locking element of the pin in a manner to prevent removal of said pin from said socket, once received therein, without damaging one or both of said parts.

7. The identification device according to claim 6, wherein said band includes a main section formed with said series of holes, and with an end section formed at one end of said main section and carrying said two parts of the fastener.

8. The identification device according to claim 7, wherein said end section is formed perpendicularly to, and at one end of, said main section of the band.

9. The identification device according to claim 8, wherein said end section is foldable along a line midway between the two parts of the fastener to permit the pin of said one part to be received through a selected hole in said main section of the band, and then through said socket in said other part of the fastener.

10. The identification device according to claim 3, wherein said fastener includes two separate fastener parts fastenable to each other through selective ones of a series of holes.

11. The identification device according to claim 10, wherein said two fastener parts are electrically connected to and within said electrically-conductive loop such that separating said fastener parts will also interrupt said electrically-conductive loop.

12. The identification device according to claim 10, wherein said two fastener parts are not electrically connected to said electrically-conductive loop such that separating said fastener parts will not interrupt said electrically-conductive loop.

13. The identification device according to claim 6 wherein said band includes a main section formed with a series of holes, and with an end section formed at one end of said main section and carrying said two parts of the fastener, and wherein said end section is formed coaxially with, and at one end of, said main section of the band.

14. The identification device according to claim 3, wherein said fastener includes two parts separate from said bracelet, one part being formed with two pins each having a locking element, the other part being formed with two sockets each for receiving a pin of said one part and having a locking recess for receiving said locking element of the respective pin in a manner to prevent removal of the pin from the socket, once received therein, without damaging one or both of said fastener parts.

15. The identification device according to claim 1, wherein said pair of electrical terminals are also designed to also serve as mounting posts for mounting a tag visually identifying the wearer.

16. The identification device according to claim 1, wherein said band is configured and dimensioned to define a bracelet to enclose and fit the wrist or ankle of the wearer.

17. The identification device according to claim 1, further including a data processor connectable to said pair of electrical terminal for establishing communication with said electronic identification chip.

* * * * *